(12) United States Patent
DiFoggio et al.

(10) Patent No.: US 7,423,258 B2
(45) Date of Patent: Sep. 9, 2008

(54) METHOD AND APPARATUS FOR ANALYZING A DOWNHOLE FLUID USING A THERMAL DETECTOR

(75) Inventors: Rocco DiFoggio, Houston, TX (US); Paul Bergren, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 116 days.

(21) Appl. No.: 11/051,388

(22) Filed: Feb. 4, 2005

(65) Prior Publication Data

US 2006/0175547 A1    Aug. 10, 2006

(51) Int. Cl.
*G01V 5/08* (2006.01)
(52) U.S. Cl. .................................. 250/269.1
(58) Field of Classification Search ............... 250/269.1
See application file for complete search history.

(56) References Cited

U.S. PATENT DOCUMENTS

| | | | |
|---|---|---|---|
| 5,204,527 A | 4/1993 | Buchanan | |
| 6,491,095 B2 | 12/2002 | Kompanek | |
| 6,627,873 B2 * | 9/2003 | Tchakarov et al. | 250/256 |
| 6,859,032 B2 * | 2/2005 | Heaton et al. | 324/303 |
| 6,874,361 B1 * | 4/2005 | Meltz et al. | 73/152.32 |
| 2003/0062472 A1 * | 4/2003 | Mullins et al. | 250/269.1 |
| 2004/0252748 A1 * | 12/2004 | Gleitman | 374/130 |
| 2005/0269499 A1 * | 12/2005 | Jones et al. | 250/269.1 |

OTHER PUBLICATIONS

Tunable, Micromachined, Electrostatic Actuated PyroMid® Band Pass Filter For The MIR Region, Jan. 26, 2004, 2 pages.

Gentile et al., "Calibration Of A Pyroelectric Detector At 10.6 µm With The National Institute Of Standards And Technology High-Accuracy Cryogenic Radiometer", Applied Optics, vol. 36, No. 16, Jun. 1, 1997, pp. 3614-3621.

IR Microsystems-Solutions For The Detection Of Infrared Light Uncooled µray Detector Series, Oct. 2001, pp. 1-4.

Tutorial Optical Meters and Detectors, Photonics, Newport, pp. 167-173, no date.

Spectrometry Modules, IR Microsystems, no date.

Hawkeye Pulsable Infrared Emitters, IR-50 Series, http://www.hawkeyetechnologies.com/ir50.htm, no date.

* cited by examiner

*Primary Examiner*—David P. Porta
*Assistant Examiner*—Mindy Vu
(74) *Attorney, Agent, or Firm*—Madan, Mossman and Sriram, P.C.

(57) ABSTRACT

The present invention provides a method and apparatus for estimating a property of a fluid downhole by exposing the fluid to modulated light downhole and sensing changes in intensity of infrared radiation from the downhole fluid to estimate the property of the downhole fluid. The present invention senses changes in intensity of light by converting the changes to transient changes in temperature of a detector, such as a pyroelectric detector. The present invention performs spectroscopic analysis of fluids by optically filtering the light allowed to impinge on a pyroelectric detector, converting the changes in temperature of the pyroelectric detector to a signal and converting the signal to estimate the property of the downhole fluid. The light source is modulated by mechanically chopping the beam or by electrically pulsing the light source or by steering the beam between different path lengths of sample or between a reference cell (filled with a reference fluid or empty) and a sample-filled cell.

35 Claims, 8 Drawing Sheets

METHOD AND APPARATUS FOR ANALYZING A DOWNHOLE FLUID USING A THERMAL DETECTOR

BACKGROUND OF THE INVENTION

1. Field of the Invention

The present invention relates generally to the field of downhole sampling and in particular to the downhole analysis of fluids and gases containing hydrocarbons using electromagnetic radiation (light) including Mid Infrared (MIR) light, Near Infrared (NIR) light and a temperature sensitive detector, such as a pyroelectric detector for measurement and estimation of properties of fluid and gas samples and properties of the reservoir from which a fluid or gas is taken, prior to, during, or after capture of the fluid or gas in a sample chamber.

2. Summary of the Related Art

In wellbore exploration, drilling mud such as oil-based mud and synthetic-based mud types are used. The filtrates from these mud types generally invade the formation through the borehole wall to an extent, meaning that these filtrates must be removed, as much as they can be removed, from the formation by pumping in order to access the formation fluids after filtrate has been pumped out. Open hole sampling is an effective way to acquire representative reservoir fluids. Sample acquisition allows determination of critical information for assessing the economic value of reserves. In addition, optimal production strategies can be designed to handle these complex fluids. In open hole sampling, initially, the flow from the formation contains considerable filtrate, but as this filtrate is drained from the formation, the flow increasingly becomes richer in formation fluid. That is, the sample flow from the formation contains a higher percentage of formation fluid as pumping continues.

It is well known that fluid being pumped from a wellbore undergoes a clean-up process in which the purity of the sample increases over time as filtrate is gradually removed from the formation and less filtrate appears in the sample. When extracting fluids from a formation, it is desirable to quantify the cleanup progress, that is, the degree of contamination from filtrate in real time. If it is known that if there is too much filtrate contamination in the sample (for example, more than about 5 or 10%), then there may be no reason to collect the formation fluid sample into a sample tank until the contamination level drops to an acceptable level. Thus, there is a need for a method and apparatus for directly analyzing a fluid sample and determining percentage of filtrate contamination in a sample.

Properties of formation fluids and gases have been determined in situ downhole using near-infrared light detection and analysis. Mid-infrared (MIR) light detection and analysis, however, has not been performed downhole even though the mid-infrared or "fingerprint" region of the spectrum is often preferable for identifying specific chemical compounds and for achieving higher sensitivity to small concentrations of chemicals. It has not been performed downhole primarily because of the difficulty of performing MIR spectroscopy in the downhole environment. The tool itself is very hot so it is continually emitting background MIR radiation, which could interfere with any readings taken by typical photodetectors. However, pyroelectric detectors respond only to changes in light intensity so they ignore any constant background of light radiation regardless of how intense such constant light is. Instead, they will respond only to a flickering light source. Another challenging part of light detection in a downhole tool (such as a downhole spectrometer) is the effect of the high downhole temperatures (up to 200 C) on typical photodetectors. For the same amount of light, the response of most photodiodes drops rapidly with increasing temperature because the internal shunt resistance of the photodiode drops as the temperature increases. The effect is exacerbated for longer wavelength photodiodes such as those sensitive to light in the 1.1 to 2.2 micron range and beyond, for example, in the MIR (2.5 to 11 micron) range. Thus, there is a need for a MIR detector suitable for use downhole.

Typically, the longer the wavelength that a photodiode can detect, the lower the photodiode's shunt resistance at room temperature. This shunt resistance drops even further at elevated temperatures. Thus there is a need for an optical detector that does not exhibit this shunt resistance problem at high downhole temperatures. Pyroelectric detectors respond to the rate of temperature change (such as that caused by absorbing a blinking light) rather than to temperature itself. Thus, pyroelectric detectors are not affected by high temperatures whenever those high temperatures are far below the detector's Curie temperature (which is 620 C for Lithium Tantalate). Light detectors are classified either as quantum detectors (photoconductors and photodiodes) or as thermal detectors (pyroelectrics, Golay cells, bolometers, thermopiles, some liquid crystals, etc.).

Quantum detectors are semiconductor devices that have a bandgap. Their conductivity changes when they absorb a photon that has enough energy to promote an electron from the valence band across the bandgap to the conduction band. The longest wavelength of light that a quantum detector can detect corresponds to light whose quantum energy is exactly equal to the bandgap energy. Mid-infrared light is low energy light so it can only be detected by small-bandgap quantum detectors. Unfortunately, the smaller the bandgap, the more likely it is that, at elevated temperatures, some electrons will have enough thermal energy to reach the conduction band even when no light is being absorbed by the detector.

Photoconductors are typically heavily N and P doped semi-conductors such as lead sulfide or lead selenide. Exposure to light creates additional conduction electrons and holes, which cause the detector's resistance to drop. A small increase in the detector's ambient temperature usually creates a comparable increase in electron-hole pairs so these detectors are usually used with modulated light.

Both PN and PIN junctions are light sensitive. Such junctions are used to make photodiodes. When used in the photovoltaic mode, a photodiode generates current when it absorbs light. When used in the photoconductive mode, a reverse bias voltage is applied to the photodiode so that, when it is absorbs light, diode resistance drops and current flows in the reverse direction through the diode.

Thermal detectors detect light from the temperature changes they undergo when they absorb or release heat. Several types of thermal detectors are described below. A pyroelectric detector's response is proportional to its rate of temperature change when it absorbs modulated light. The reason is that, when a pyroelectric material is heated by a light pulse, its dipole moment changes, and while its dipole moment is changing, there is a temporary flow of current. A steady light produces no pyroelectric detector response regardless of the light's intensity.

A Golay cell is a thermal detector based on photoacoustics. Conceptually, it is a sealed, gas-filled box that absorbs light. Modulating the light causes pressure pulses in the gas within the Golay cell and these pressure pulses are picked up by a microphone. A steady light produces no Golay cell response regardless of the light's intensity.

A bolometer is a device whose electrical resistance changes due to heating caused by absorbing light. The two types of bolometers are the barretter (for which electrical resistance increases with increasing temperature) and the thermistor (for which electrical resistance decreases with increasing temperature). The term "thermistor" is often used to refer to both barretters and traditional thermistors. The qualifiers, "positive thermal coefficient" and "negative thermal coefficient", respectively, are used to distinguish between the opposite directions of resistance change with increasing temperature.

A thermopile is a group of thermocouples connected in series. Each thermocouple is a junction of dissimilar metals that produces a voltage when one side of the junction is at a different temperature than the other side. A liquid crystal thermal detector makes use of the temperature-dependence of a liquid crystal's light scattering properties. The detector can be a thin plastic strip, covered with liquid crystals such as the disposable medical thermometers that are placed on a person's forehead.

Thermal detectors such as bolometers, thermopiles, and liquid crystals, generate a large steady-state signal due to the ambient temperature (or due to an above-ambient temperature caused by absorbing steady-state light) and a small modulated signal from transient heating caused by absorbing modulated light. Thus, they respond to background infrared radiation, steady-state infrared light, and to modulated infrared light. In principle, such thermal detectors could also be used to detect modulated infrared light in the hot downhole environment by processing their signal to remove the steady-state component and recover only the modulated component.

Thermal-change detectors, such as pyroelectric detectors and Golay cells, are probably more suitable than other thermal detectors for use as infrared light detectors in the hot downhole environment because thermal-change detectors generate no signal from the high ambient temperature or from steady-state light but respond only to modulated light.

SUMMARY OF THE INVENTION

The present invention provides a method and apparatus for estimating a property of a fluid downhole by exposing the fluid to modulated light (electromagnetic radiation) and sensing changes in intensity of radiation from the fluid to estimate the property of the fluid. Radiation from the fluid includes but is not limited to emission, transmission, absorption, luminescence and reflection from the fluid. A processor is configured or programmed to estimate a property of the fluid from the changes in intensity of radiation from the fluid. For chemical analysis, infrared light offers some advantages over other wavelength regions. Other wavelength regions can also be used to estimate properties of a downhole fluid. Pyroelectric detectors can sense modulated light over an extraordinarily wide wavelength range for which the wavelength varies by a factor of 100,000. This range includes vacuum-ultraviolet (10-200 nm), ultraviolet (200-400 nm), visible (400-700 nm), near-infrared (700-2500 nm), mid-infrared (2.5-20 microns), and far-infrared (20-1000 microns), which borders on microwaves.

By contrast, photodiodes span a much narrower wavelength range for which wavelength varies by only a factor of two or three. The present invention senses changes in intensity of infrared light by converting the changes in light intensity to changes in temperature using a sensor, such as a pyroelectric detector.

The present invention performs spectroscopic analysis of fluids by optically filtering the light that impinges on a optically or thermally sensitive detector, such as a pyroelectric detector, converting the rate of temperature change to a signal, and converting and analyzing the signal to estimate the property of the downhole fluid. When two objects of different temperatures are arranged so that they can exchange photons with each other, the hotter object will radiate more photons to the cooler object than the cooler object radiates back to the hotter object. The cooler object warms as the hotter object cools so both objects change temperature. Therefore, when collecting infrared spectra using a temperature-change detector, such as a pyroelectric detector, it is possible to use either an infrared light "source" or an infrared light "sink".

That is, infrared spectra associated with the downhole fluid can be collected by interposing both a fluid and a shutter between a pyroelectric detector that is at one temperature and an object that is either at a higher temperature (a light source) or at a lower temperature (a light sink) than the pyroelectric detector. This can be confirmed experimentally using ice as a light sink for collecting infrared spectra using a pyroelectric array at room temperature. The infrared light source or sink is modulated by pulsing, interrupting, or chopping infrared light from a light source typically at about 10 Hz. Transmission or attenuated reflectance spectra can be collected downhole, where transmission spectra would primarily be collected for gases and vapors and attenuated reflectance spectra would primarily be collected for liquids.

Modulation can also involve steering the light source's beam so as to rapidly alternate between passing the beam through an empty (reference) cell and passing the beam through a sample-filled cell before the beam strikes the pyroelectric detector. Modulation could also involve steering the light source's beam so as to rapidly alternate between passing the beam through a short-pathlength sample-filled cell and passing the beam through a long-pathlength sample-filled cell before the beam strikes the pyroelectric detector. Alternatively, one of the path lengths, either long or short, can be a path through a vacant or empty cell. In the case where one path is empty and the other sample-filled, the path lengths can be the same length. The present invention provides a high gain amplifier for amplifying the signal associated with the sensed changes in temperature in a high-gain high-temperature circuit. The infrared light includes but is not limited to light in the wavelength range of 1.0 to 11 microns.

The spectroscopic analysis includes estimating presence of a gas in a downhole fluid, which includes estimating ratios such as the ratio of C1, C2, C3, C4, and C5 or other gases in the downhole fluid. In this notation, C1 means methane (1 carbon atom), C2 means ethane (2 carbon atoms), and so on. Spectroscopic analysis also includes estimating of parts per million of $H_2S$ in the downhole fluid. The present invention applies a soft modeling technique to the spectroscopic analysis to estimate a physical characteristic or a chemical characteristic of the downhole fluid or gas. The physical characteristic includes density and viscosity of the downhole fluid. The chemical characteristic includes composition of the fluid or gas. The present invention also estimates formation cleanup from a series of property determinations (e.g., successive viscosity estimates) of the downhole fluid or from a direct estimation of the percentage of filtrate contamination in the downhole fluid.

BRIEF DESCRIPTION OF THE FIGURES

For a detailed understanding of the present invention, references should be made to the following detailed description of an embodiment, taken in conjunction with the accompanying drawings, in which like elements have been given like numerals, wherein.

DETAILED DESCRIPTION OF THE INVENTION

The present invention provides in one embodiment, a downhole infrared spectrometer using a detector such as a pyroelectric detector to enable spectral measurements from which estimates of the physical and chemical properties of a downhole fluid are made. The pyroelectric detector is provided in one embodiment to measure mid-infrared light downhole. Unlike photodiodes, pyroelectric detectors are based on a different principle so that the pyroelectric detectors do not have a shunt resistance problem at high temperatures downhole. Pyroelectric detectors are commonly used in the infrared motion detectors that automatically open the doors to a grocery store as a person approaches. Changes in the amount of light striking a pyroelectric detector cause miniscule, transitory changes in the detector temperature that generate a transient signal. This signal is not affected by the temperatures of the surroundings or by the detector's own temperature, provided that the detector temperature is well below the Curie temperature.

The Curie temperature is usually relatively high, such as 620 degrees Centigrade for Lithium Tantalate pyroelectric detectors. Pyroelectric detectors respond equally well to almost all wavelengths of light from ultraviolet to visible to mid-infrared and far infrared and their response does not degrade with temperature. Pyroelectric detectors provide signals that are much smaller than those of photodiodes. High-gain circuitry may be utilized to boost the signals associated with pyroelectric detectors. Pyroelectric detectors are only one example of a thermal detector suitable for use in detecting changes in intensity of electromagnetic radiation including all frequencies of light including but not limited to NIR, MIR, visible light and microwave.

The present invention provides one pyroelectric detector or a pyroelectric detector array with high gain circuitry. A linear variable mid-infrared optical filter (which is a filter whose transmitted wavelength varies linearly from one end to the other) is placed over the pyroelectric array so that light incident upon the pyroelectric detector is passed through the linear variable filter before impinging the pyroelectric detector. In the context of this specification, the term light is used in its broadest physical sense to include all electromagnetic radiation including but not limited to NIR, MIR, visible light and microwave energy. Alternatively, single-color optical filters could be placed over each of a series of individual pyroelectric detectors. The pyroelectric array itself is substantially unaffected by high temperature, however, a sorption cooling unit may be provided to cool electronics such as the high gain circuitry associated with the pyroelectric array.

Figure 1:
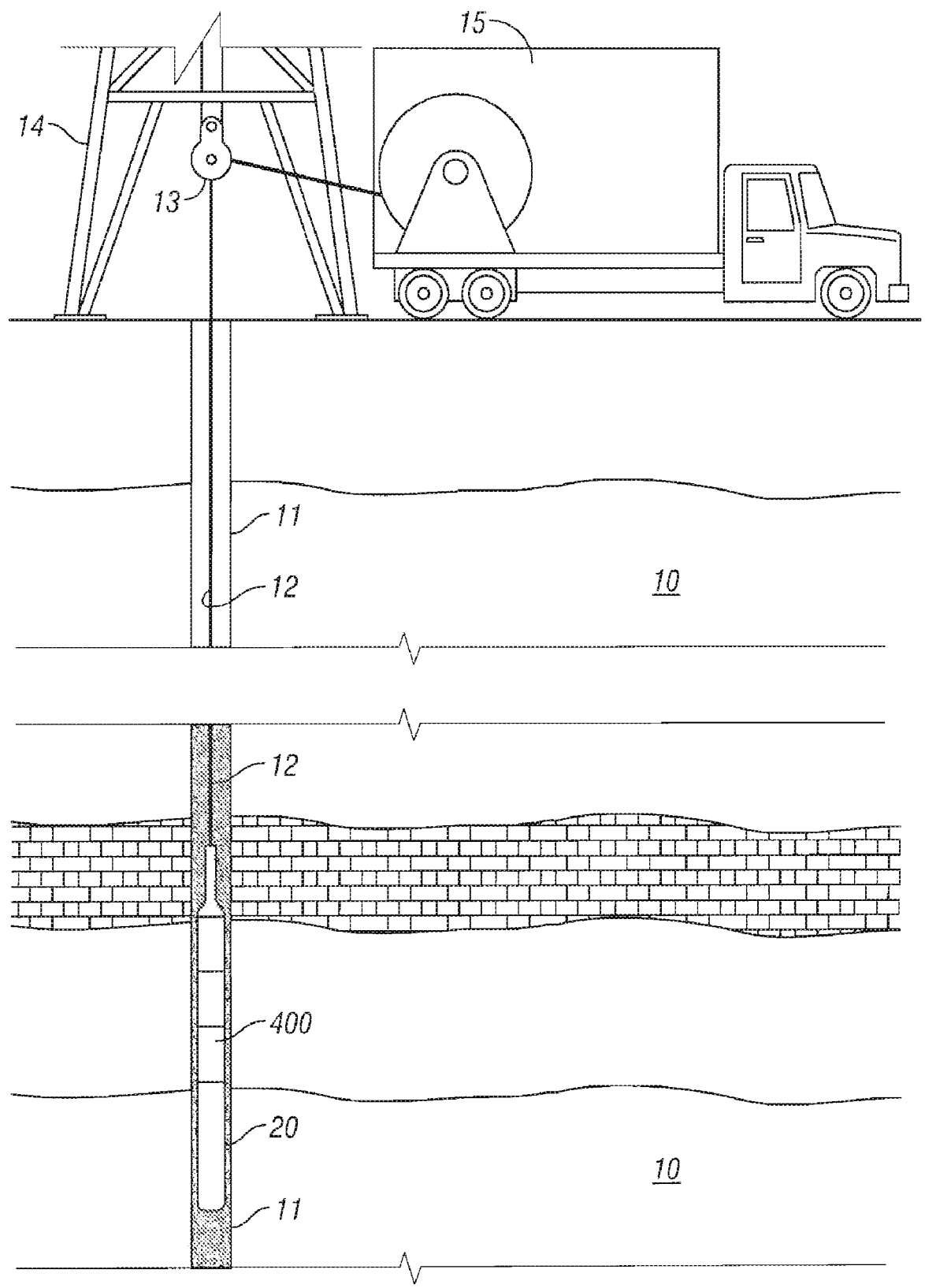
FIG. 1 is a schematic of an installation illustrating the invention operating environment.

Turning now to FIG. 1, FIG. 1 schematically represents a cross-section of earth 10 along the length of a wellbore penetration 11. Usually, the wellbore will be at least partially filled with a mixture of liquids including water, drilling fluid, and formation fluids that are indigenous to the earth formations penetrated by the wellbore. Suspended within the wellbore 11 near the bottom end of a drill string or wireline 12 is a formation fluid sampling tool 20. The present invention 400 is included on sampling tool 20. The wireline 12 is often carried over a pulley 13 supported by a derrick 14. Wireline deployment and retrieval is performed by a powered winch carried by a service truck 15, for example.

Figure 2:
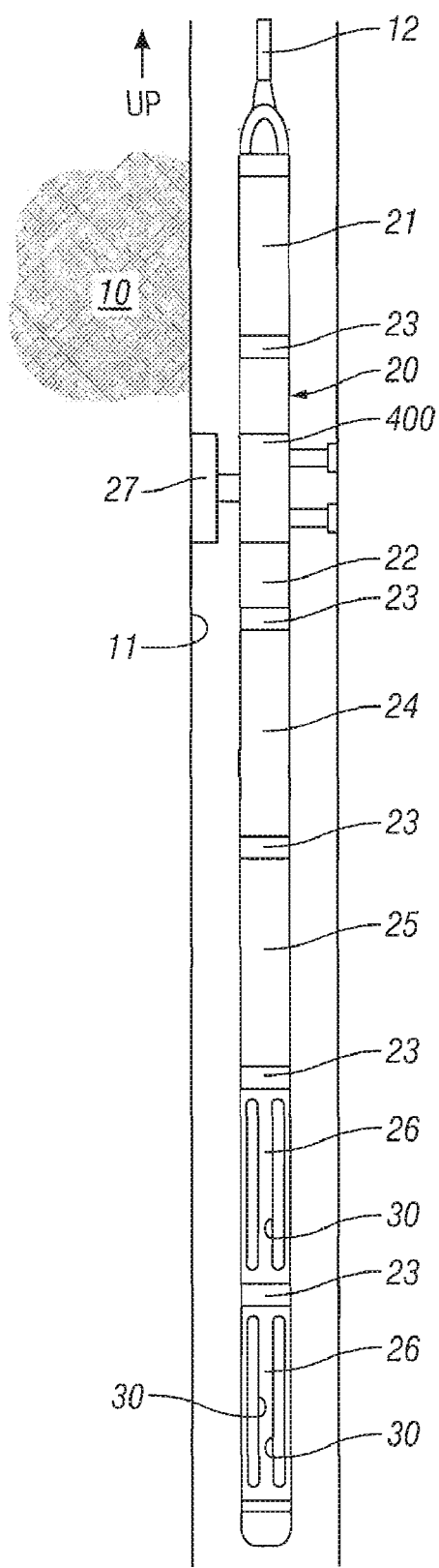
FIG. 2 is a schematic of the invention in operative assembly with cooperatively supporting tools.
Figure 3:
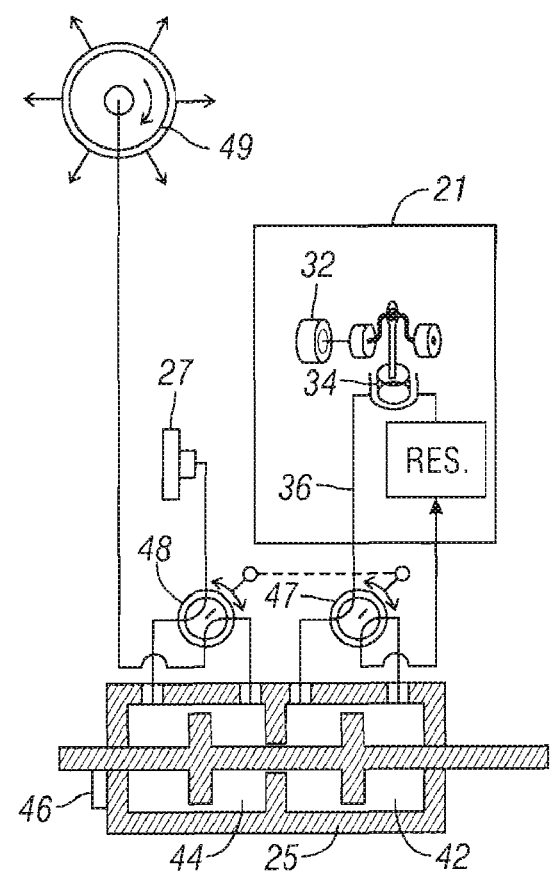
FIG. 3 is an illustration of a pump used in an embodiment of the present invention.

Pursuant to the present invention, an exemplary embodiment of a sampling tool 20 which includes the present invention 400 is schematically illustrated by FIG. 2. Preferably, such sampling tools comprise an assembly of several tool segments that are joined end-to-end by the threaded sleeves or mutual compression unions 23. An assembly of tool segments appropriate for the present invention may include a hydraulic power unit 21 and a formation fluid extractor 22. Below the extractor 22, a large displacement volume motor/pump unit 24 is provided for line purging. Below the large volume pump is a similar motor/pump unit 25 having a smaller displacement volume that is quantitatively monitored as described more expansively with respect to FIG. 3. Ordinarily, one or more sample tank magazine sections 26 are assembled below the small volume pump. Each magazine section 26 may have three or more fluid sample tanks 30.

Figure 4:
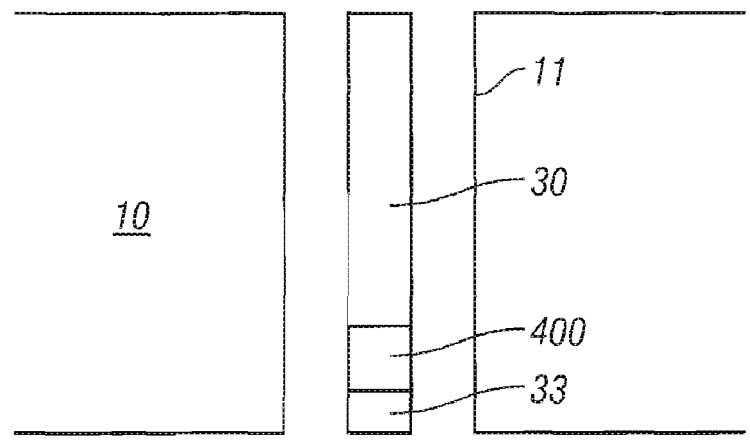
FIG. 4 is an illustration of the present invention deployed from a drill string in an embodiment of the present invention.

The formation fluid extractor 22 comprises an extensible suction probe 27 that is opposed by bore wall feet 28. Both, the suction probe 27 and the opposing feet 28 are hydraulically extensible to firmly engage the wellbore walls. Construction and operational details of the fluid extraction tool 22 are well known and more expansively described by U.S. Pat. No. 5,303,775. The present invention can also be deployed from a drill string 30 behind a drill bit 33 as shown in FIG. 4.

In the present invention, pyroelectric detectors are made of a ferroelectric crystal which has a permanent dipole moment. When subjected to an optical pulse, the crystal is heated, which causes the dipole moment to change. The changing of this dipole moment causes a current to flow, which is converted to a voltage in the detector head that can be measured by an optical power meter, oscilloscope or in the case of the present invention analyzed by a spectrometer downhole.

The present invention is useful for, but not limited to, estimating a property of a downhole fluid, for example, providing mid-infrared spectroscopy for trace gas analysis such as parts per million of H2S extracted from live crude oil or estimating the ratios of C1, C2, C3, C4 and C5 or other gases in a downhole fluid. The present invention provides a solution for, among other things, the difficulties of providing mid-infrared (wavelengths greater than, for example, 2.5 microns) downhole at high temperatures by eliminating the shunt resistance problem experienced by photodiodes. The inventors are not aware of mid-infrared photodiodes that can produce usable signals at high downhole temperatures, for example, above 150 degrees centigrade. In one aspect of the invention provides a pyroelectric detector which measures mid-infrared light downhole at temperatures of 250 degrees centigrade and more.

In addition to the temperature problems experienced downhole, there is also a steady ambient background of mid-infrared black-body radiation from the downhole tool and its surroundings. This steady ambient background of mid-infrared radiation interferes with conventional steady state measurement of infrared energy. Pyroelectric detectors respond to changes in light intensity, and thus are insensitive or "blind" to any constant background infrared radiation such as the black-body ambient radiation in the hot downhole environment that would otherwise interfere with infrared measurements. The present invention provides a modulated light source to provide changes in light intensity to which the pyroelectric detector does respond.

Figure 5:
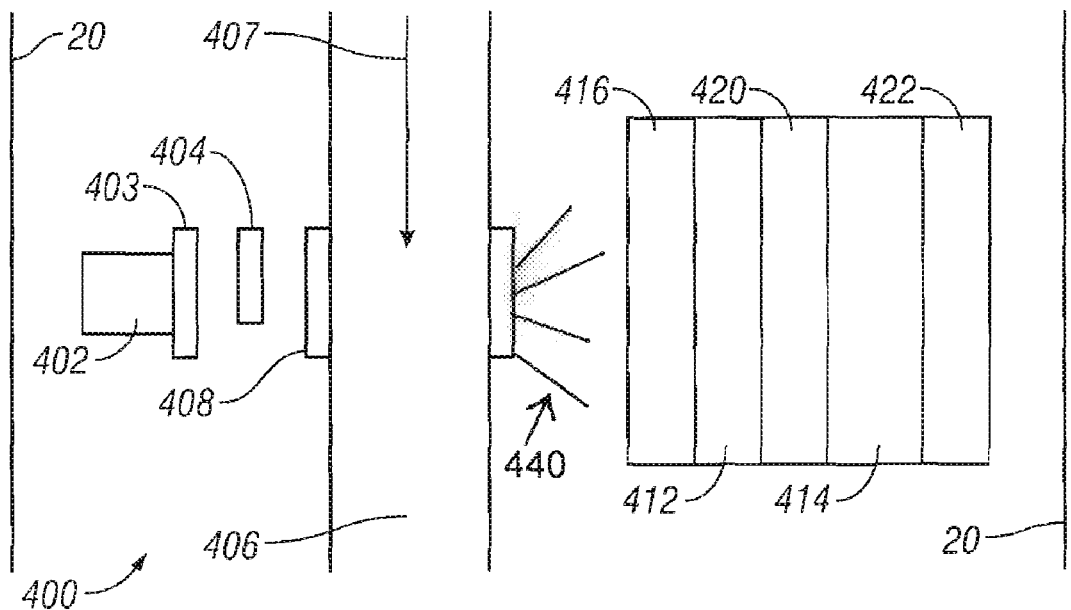
FIG. 5 is a schematic diagram of an embodiment of the present invention.

Turning now to FIG. 5, a schematic of an example in one aspect of the present invention 400 is presented. In one embodiment, the present invention 400 comprises a light source 402, such as an infrared light source which can be a steady state light source or a modulated or pulsed light source. In the case of a steady state light source a light modulator is provided. The modulator can be any suitable device which varies the intensity of the light source, including but not limited to an electronic pulser circuit, well known in the art, that varies the intensity of the light source or an electromechanical chopper 404 that interrupts the path of the light source to the downhole fluid. The modulator is provided to modulate the intensity of light from the light source that impinges on the fluid and the photodetector. A reflector or collimator 403 can be provided to focus and/or concentrate light from the light source 402. A chamber or conduit 406 is provided for presentation of a downhole fluid for exposure of the downhole fluid to light from the light source. An optical window 408 is provided, through which the downhole fluid 407 is exposed to the light. For purposes of the present application, the term "fluid" includes liquids, gases and solids that may precipitate from a fluid or a gas.

The present invention further includes a detector such as a pyroelectric detector 412. The pyroelectric detector 412 can also comprise a pyroelectric detector array. A spectrometer 414 and processor 422 are provided for analyzing signals from the pyroelectric detector to determine a property of the fluid 407 downhole. A mid-infrared linear variable filter 416 is provided and interposed between light radiating 440 from the downhole fluid and the pyroelectric detector 412. A high gain amplifier 420 is provided to amplify the signal from the pyroelectric detector 412 when desired. The spectrometer 414 includes a processor 422 with memory. The processor 422 includes programs that implement soft modeling techniques for applying a chemometric equation, neural network or other soft modeling programs to the measurements of infrared light detected by the pyroelectric detector to estimate other physical and chemical properties of the downhole fluid from the pyroelectric detector signal. The spectrometer output responsive to the pyroelectric signal is also input to the soft modeling program, neural network or chemometric equation to estimate properties of the downhole fluid.

Many pyroelectric detectors are suitable for use with the present invention, once adapted for downhole use. One example of a pyroelectric detector, among many others, believed to be suitable for downhole use is the pyroelectric detector available from IR Microsystems, PSE-C, CH-1015 Lausanne, Switzerland, telephone 41-21-693 8528. The IR Microsystems detector provides a high end read out application specific integrated circuitry (ASIC). A spectrometer is also available from IR Microsystems.

Many light sources are suitable for use with the present invention, once adapted for use downhole. One example of a light source, among many others, believed suitable for downhole use is the pulsed infrared emitter available from Hawkeye Technologies. The Hawkeye infrared emitter works up to 500-750 degrees Centigrade.

A sorption cooling unit 423 is provided to keep heat sensitive electronics such as the high-gain amplifier section of the spectrometer within a safe operating temperature, when desired. The sorption cooling unit is described in U.S. Pat. No. 6,672,093 entitled "Downhole Sorption Cooling in Wireline Logging and Monitoring While Drilling" by Rocco DiFoggio.

The pyroelectric spectrometer enables the present invention to perform spectroscopy downhole during or prior to sampling, after sampling or at the surface. Sorption cooling unit 423 is provided if needed adjacent the pyroelectric spectrometer and other electronics downhole as necessary to obviate the adverse affects of downhole temperatures.

Figure 6:
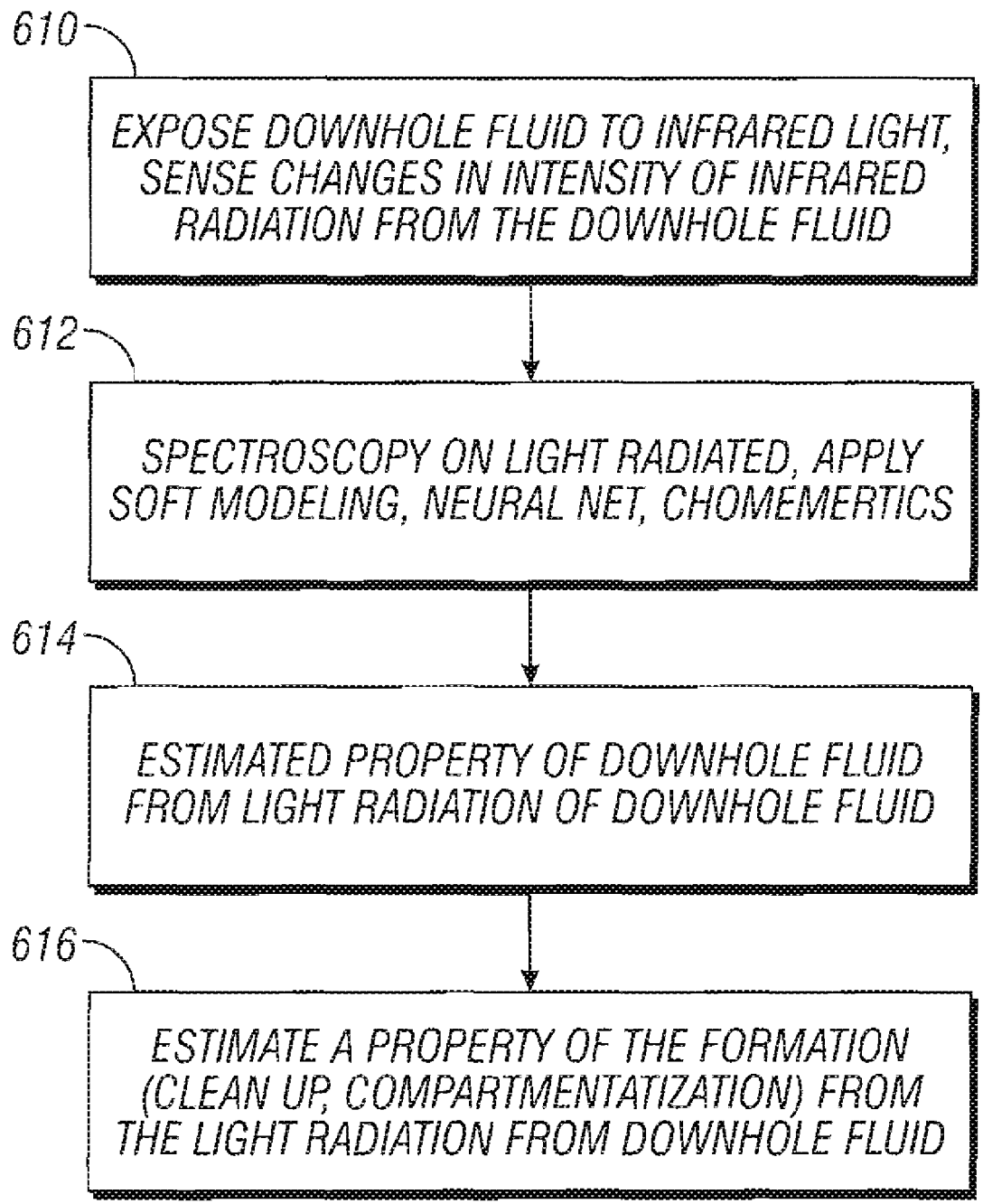
FIG. 6 is a flow chart illustrating functions performed in an embodiment of the present invention.

FIG. 6 is a flow chart describing the process for analyzing a formation fluid downhole. In 610 the downhole fluid is exposed to light or electromagnetic radiation, including but not limited to, infrared light. The pyroelectric detector senses changes in intensity from light radiated from the downhole fluid. In 612 the processor and spectrometer perform spectroscopy of the infrared radiation from the downhole fluid and applies soft modeling, a neural network or chemometrics to the spectra. The processor reads the output of the pyroelectric spectrometer to determine a physical or chemical property of the sample of downhole fluid. In 614 the programmed processor estimates a property of the downhole fluid from the light radiation from the downhole fluid. In 616 the programmed processor estimates a property of the formation, such as formation clean up or compartmentalization from the light radiation from the downhole fluid.

Samples of downhole fluid are taken from the formation by pumping fluid from the formation through a flow line and into a sample cell. Filtrate from the borehole normally invades the formation and consequently is typically present in formation fluid when a sample is drawn from the formation. As formation fluid is pumped from the formation the amount of filtrate in the fluid pumped from the formation diminishes over time until the sample reaches its lowest level of contamination. This process of pumping to remove sample contamination is referred to as sample clean up. In one embodiment, the present invention indicates that a formation fluid sample clean up is complete (contamination has reached a minimum value) when the quantity of filtrate detected has leveled off or become asymptotic within the resolution of the measurement of the tool for a period of twenty minutes to one hour.

The pyroelectric spectrometer provided by the present invention can be used to estimate a property of the formation or reservoir from which the downhole fluid came, or a property of a downhole fluid sample, such as filtrate contamination by detecting the dominant chemical used in the base oil of the filtrate (particularly when its mid-infrared spectrum is very different from that of most crude oils as is the case for many synthetic base oils) or by detecting any of the chemicals added to the base oil, such as the emulsifiers, surfactants, or fluid loss materials. A sample of well bore fluid can be taken to determine an identifying characteristic of the well bore fluid.

The pyroelectric spectrometer can also be used to estimate trace amounts of gases such as H2S, or, using spectral correlations to known samples, to estimate trace amounts of metals, such as mercury, nickel or vanadium in either crude oil or formation brines for particular fields or basins. Furthermore, the present invention can be used to estimate subtle differences in the chemical composition of two samples of crude oil obtained from different depths or sections in the well that could be used as an indicator that those sections are compartmentalized from one another.

Compartmentalization is another formation parameter estimated by the present invention. Multi-billion dollar decisions on how to develop a reservoir (well locations, types of production facilities, etc.) are based on whether or not a reservoir is compartmentalized. As the name implies, compartmentalization of a reservoir simply means that different sections of a reservoir are separate compartments across which fluids do not flow. Separate compartments must be drained separately (requiring additional wells) and may need different types of processing for their fluids. In like manner, it can be important to assess reservoir compartmentalization of aqueous zones when planning waste water injection wells.

An example of a subtle chemical difference that could be indicative of compartmentalization would be a change in the ratio of trace hydrocarbons such as phytane/pristine. Any other unexpected compositional differences could also indicate compartmentalization. Gravity segregation will cause some expected spectral differences in fluids from different depths even when there is no compartmentalization. For example, one expects the top of a column of crude oil to have a higher concentration of natural gas dissolved in it than does the bottom of the column. Thus, by comparing a composition for a first fluid or gas taken at one point in a formation or reservoir to a second fluid or gas taken at a second point in a formation or reservoir, an estimation can be made as to the compartmentalization of the reservoir or formation, by a comparison or differentiation between the composition for the first fluid or gas and the composition of the second fluid or gas. If the first fluid or gas has substantially the same composition as second fluid or gas, the reservoir is connected and not compartmentalized.

Figure 7:
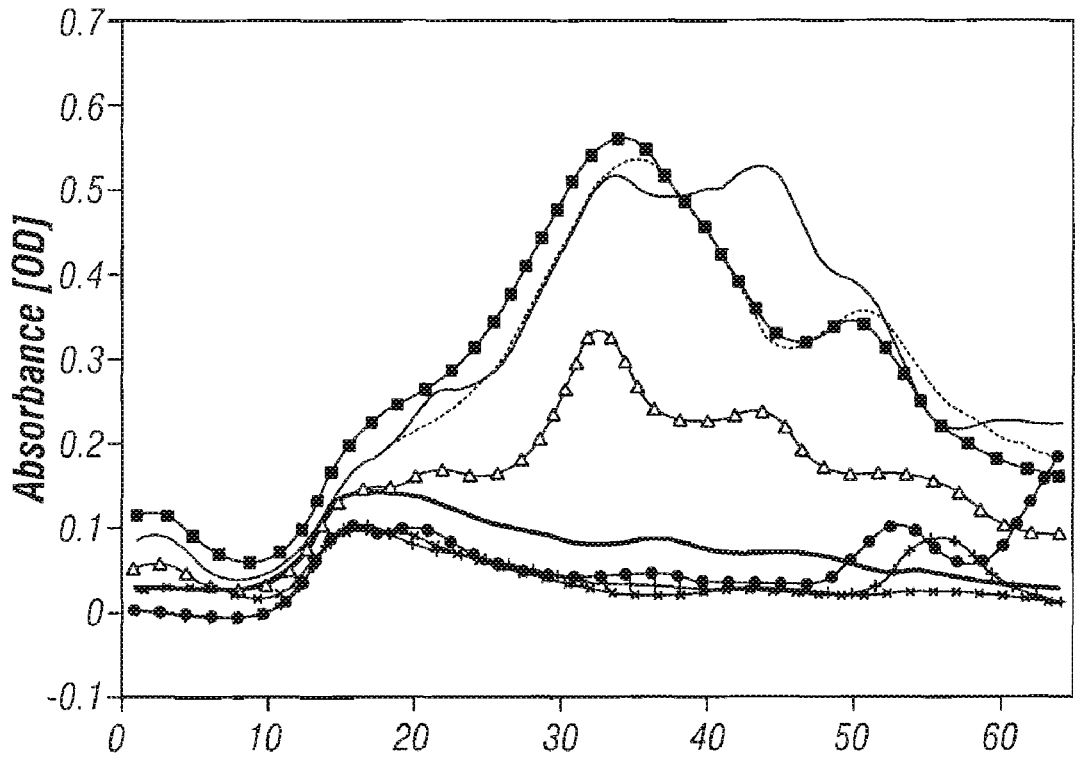
FIG. 7 compares the 64-channel pyroelectric-array mid-infrared absorption spectrum of a crude oil (the smooth line without data-point markers) to the mid-infrared spectra of 12 different base oils commonly used in oil-based muds over the wavelength range of approximately 5 microns to 11 microns in an embodiment of the present invention.
Figure 7:
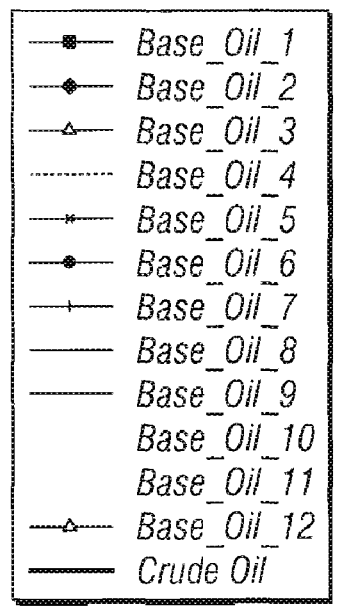

FIG. 7 compares the 64-channel pyroelectric-array mid-infrared absorption spectrum of a crude oil 700 (the smooth line without data-point markers) to the mid-infrared spectra of 12 different base oils commonly used in oil-based muds over the wavelength range of approximately 5 microns to 11 microns.

Figure 8:
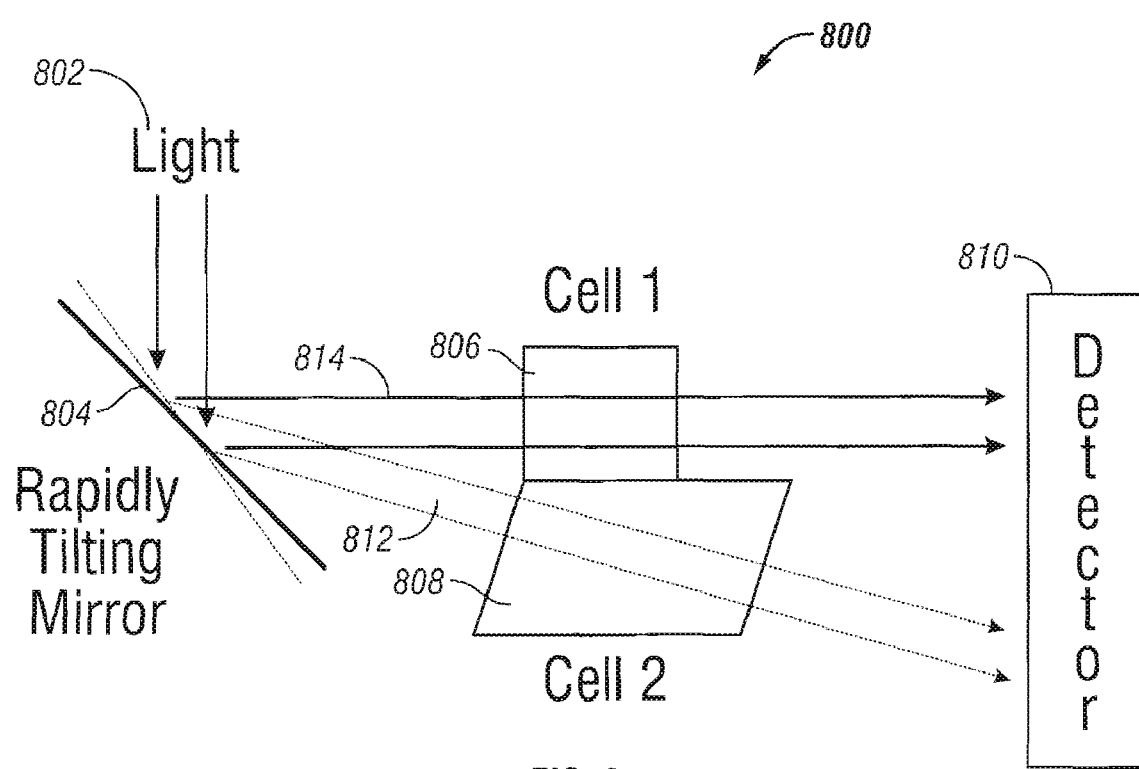
FIG. 8 illustrates a beam steering light modulation apparatus in an embodiment of the invention.

FIG. 8 illustrates a beam steering light modulation apparatus 800 in an embodiment of the invention. Modulation of the light can be achieved by steering the light beam 802 using a rapidly tilting mirror 804 so that it rapidly alternates between either passing through Cell 1 806 as beam 814 or through Cell 2 808 as beam 812 before striking the detector 810. For example, Cell 2 can contain a fluid sample while Cell 1 can serve as a reference cell that is either empty or contains a shorter pathlength of fluid sample than Cell 2. When the cells contain the same fluid but have different pathlengths, the absorbance of the fluid over a distance equal to the pathlength difference is the base ten logarithm of the ratio of the light intensity transmitted through the shorter cell to the light intensity transmitted through the longer cell.

Figure 9:
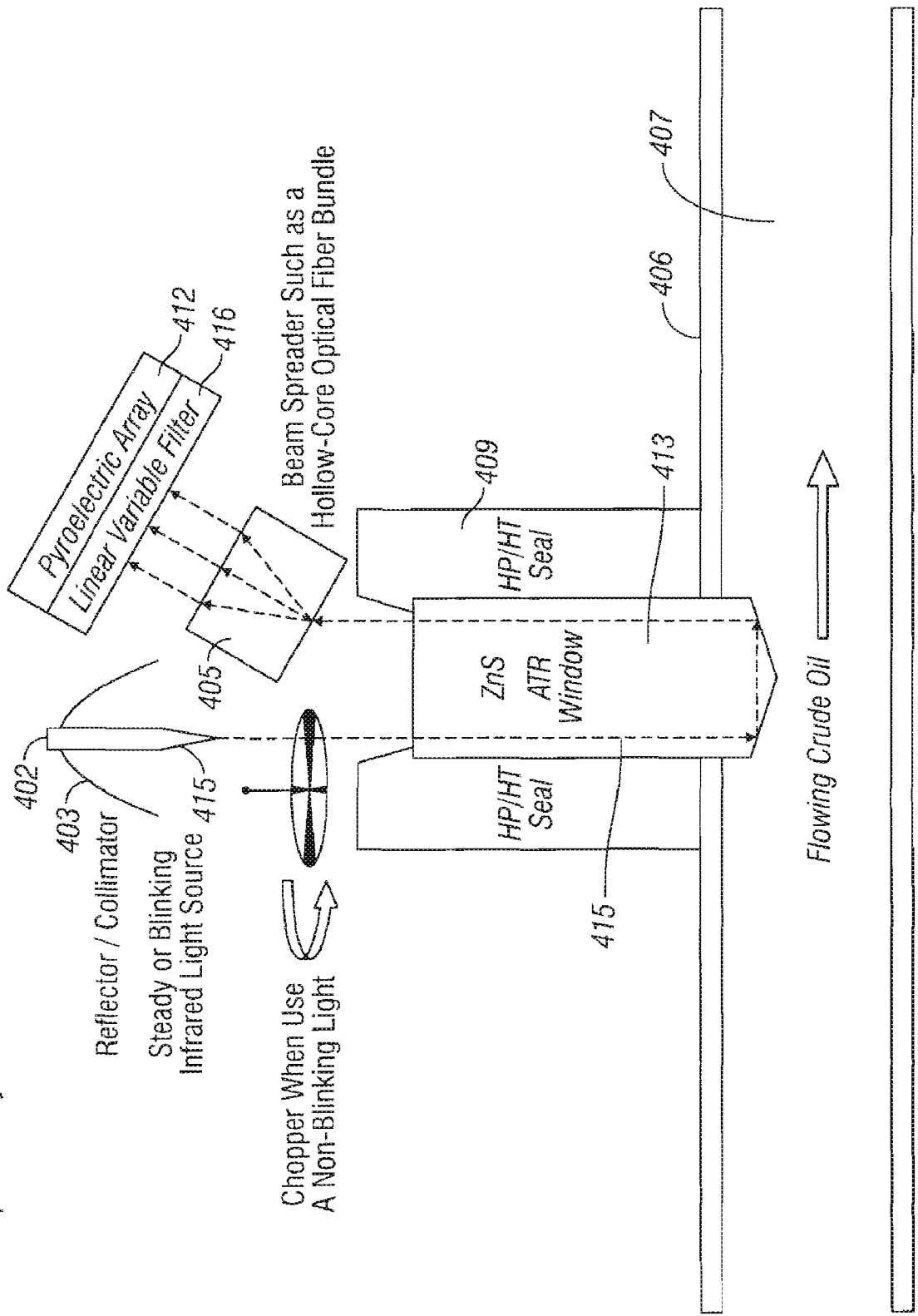
FIG. 9 illustrates an embodiment of the present invention utilizing an attenuated reflectance window in a fluid.

FIG. 9 illustrates an embodiment of the present invention utilizing an attenuated reflectance window in a fluid. As shown in FIG. 9 light source 402 is concentrated by a reflector or collimator 403. Light 415 is directed toward modulator/chopper 406. The modulated light passes through attenuated reflectance (ATR) window 413 and reflects off of flowing crude oil 407 flowing in conduit 406. The ATR window is held in place by a high pressure/high temperature seal 409. The reflected light is received by a beam spreader such as a hollow-core optical fiber bundle 405. The light passes through the beam spreader and linear variable filter 416 before being received by pyroelectric array 412.

Figure 10:
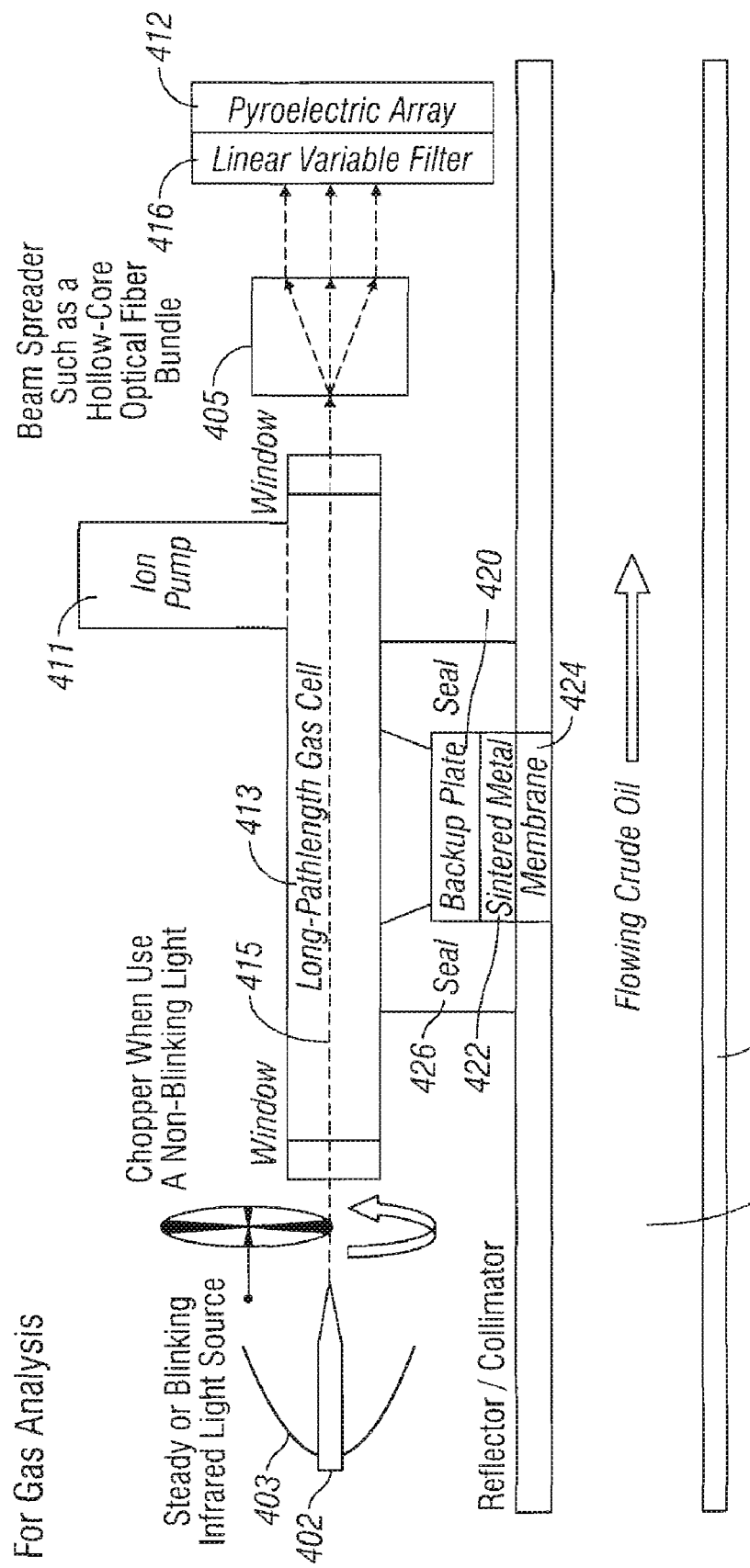
FIG. 10 illustrates an embodiment of the present invention utilizing a long-pathlength gas cell and a diffusion membrane.

FIG. 10 illustrates an embodiment of the present invention utilizing a long-pathlength gas cell and a diffusion membrane. As shown in FIG. 10, in an alternative embodiment, the present invention provides a long-pathlength gas cell 413 through which concentrated light 415 passes. Each end of the long-pathlength gas cell is capped with a window 408. Gas is diffused into the long-pathlength gas cell 413 from flowing crude oil 407 through membrane 424. The membrane is structurally supported by a sintered metal cap 422 and a porous back up plate 420. The gas cell 413 need not be long-pathlength, when the gas is dense or when one uses mirrors at both ends of the cell (White cell configuration) to increase the effective pathlength by a factor of fifty or more. In the present example a cell length of 25 centimeters is provided. The light 415 passes through the gas in the gas cell after which is passes through beam spreader 405 and linear variable filter 416 and is incident upon pyroelectric array 412. Ion pump 411 removes gas from the gas cell after measurement in the gas cell.

While the foregoing disclosure is directed to the preferred embodiments of the invention various modifications will be apparent to those skilled in the art. It is intended that all variations within the scope of the appended claims be embraced by the foregoing disclosure. Examples of the more important features of the invention have been summarized rather broadly in order that the detailed description thereof that follows may be better understood, and in order that the contributions to the art may be appreciated. There are, of course, additional features of the invention that will be described hereinafter and which will form the subject of the claims appended hereto.

What is claimed is:

1. A method for estimating a property of a fluid downhole, comprising:
   exposing the fluid to a modulated light downhole; and
   using a thermal detector to sense a modulated light that impinged the fluid to estimate the property of the fluid.

2. The method of claim 1, wherein the thermal detector is at least one of a pyroelectric detector, Golay cell, bolometer, thermopile and liquid crystal.

3. The method of claim 1, further comprising:
   converting the changes in temperature of the thermal detector to a signal; and
   performing a spectroscopic analysis of the signal to estimate the property of the fluid.

4. The method of claim 3, further comprising:
   applying a soft modeling technique to the spectroscopic analysis to estimate at least one of a physical characteristic and a chemical characteristic of the fluid.

5. The method of claim 4, wherein the physical characteristic includes viscosity of the fluid.

6. The method of claim 1, wherein the modulating includes at least one of chopping the light, pulsing the light and steering the light between a first path and a longer second path.

7. The method of claim 1, wherein the property comprises a presence of a gas in the fluid.

8. The method of claim 1, wherein the property comprises an amount of gas.

9. The method of claim 1, wherein the property includes an amount of $H_2S$ in the fluid.

10. The method of claim 1, wherein the property of the fluid is contamination of the fluid.

11. The method of claim 1, wherein the light includes light at a frequency in a mid infrared light frequency range.

12. The method of claim 1 wherein the thermal detector is configured to detect light from a temperature change of the thermal detector.

13. The method of claim 1 wherein the thermal detector is configured to be substantially non-responsive to a steady state temperature and responsive to a change in temperature of the thermal detector.

14. A method for estimating a property of a fluid downhole, comprising:
   exposing the fluid to light downhole;
   using a thermal detector to sense a change in intensity of radiation from the fluid to estimate the property of the fluid, wherein the property comprises at least one of the set comprising ratios of C1, C2, C3, C4, and C5 gases in the fluid.

15. A method for estimating a property of a fluid downhole, comprising:
   exposing the fluid to light downhole;
   using a thermal detector to sense a change in intensity of radiation from the fluid to estimate the property of the fluid; and estimating reservoir compartmentalization from the estimate of the property of the fluid.

16. A method for estimating a property of a fluid downhole, comprising:
   exposing the fluid to light downhole;
   using a thermal detector to sense a change in intensity of radiation from the fluid to estimate the property of the fluid; and amplifying a signal associated with the sensed changes in temperature in a high-gain high-temperature circuit.

17. A fluid analyzer for determining a property of a fluid downhole, comprising:
   a modulated light source illuminating the fluid downhole;
   a thermal light sensor in optical communication with the fluid for sensing a modulated light that impinged the fluid to estimate the property of the fluid; and
   a processor in data communication with the thermal light sensor wherein the processor is configured to estimate the property of the fluid.

18. The fluid analyzer of claim 17, wherein the thermal light sensor includes a thermal detector.

19. The fluid analyzer of claim 17, wherein the modulator includes at least one of a chopper, a circuit for pulsing the intensity of the modulated light and a beam steering device.

20. The fluid analyzer of claim 17, further comprising:
   a spectrometer for analyzing the changes in intensity of the light.

21. The fluid analyzer of claim 20, wherein the analyzing includes detecting presence of a gas in the fluid.

22. The fluid analyzer of claim 20, further comprising:
   a processor for performing a soft modeling technique to an output from the spectrometer to determine at least one of a physical characteristic of the fluid and a chemical characteristic of the fluid.

23. The fluid analyzer of claim 17, wherein the light source provides a light having a frequency in a mid-infrared frequency range.

24. The fluid analyzer of claim 17, wherein the light source provides a light having a wavelength greater than 0.1 micrometers.

25. A fluid analyzer for determining a property of a fluid downhole, comprising:
   a light source illuminating the fluid downhole;
   a thermal light sensor in optical communication with the fluid for sensing changes in intensity in light associated with the fluid;
   a processor in data communication with the thermal light sensor wherein the processor is configured to estimate the property of the fluid, wherein the analyzing includes detecting the presence of a gas in the fluid; and wherein the detecting presence of the gas includes determining of at least one of the set of ratios of C1, C2, C3, C4, and C5 gases in the fluid.

26. The fluid analyzer of claim 25, wherein the analyzing includes estimating formation cleanup.

27. A system for estimating a property of reservoir, comprising:
   a tool for deployment in a wellbore through a reservoir;
   a modulated light source on the tool for directing light downhole towards a first fluid from the reservoir; and
   a sensor for sensing a modulated light that impinged the first fluid for determining the property of the reservoir.

28. The system of claim 27, further comprising:
   a spectrometer for analyzing the changes in intensity of different wavelengths of the light associated with the fluid.

29. The system of claim 27, wherein the light source provides a light having a frequency in a mid-infrared frequency range.

30. The method of claim 27, further comprising:
   exposing a second fluid from the formation to light downhole; and
   sensing changes in intensity of radiation from the second fluid to estimate a property of the first fluid.

31. A system for estimating a property of reservoir, comprising:
   a tool for deployment in a wellbore through a reservoir;
   a light source on the tool for directing light downhole towards a first fluid from the reservoir; and
   a sensor for sensing changes in intensity in light associated with the first fluid for determining the property of the reservoir wherein the sensor includes a pyroelectric photo detector for sensing the changes in intensity in the light associated with the fluid.

32. A method for estimating a property of a fluid downhole, comprising:
   exposing the fluid to light downhole;
   sensing a change in intensity of radiation from the fluid using a thermal detector;
   exposing a second fluid to light downhole; and
   sensing a change in intensity of radiation from the second fluid to estimate a property of the first fluid wherein the property of the first fluid is a differentiation to a second fluid from the reservoir.

33. The method of claim 32, wherein the property of the reservoir is compartmentalization.

34. A method for estimating a property of a fluid downhole, comprising:
   exposing the fluid to a light downhole; and
   using a thermal detector to sense changes in intensity of radiation from the fluid to estimate the property of the fluid, wherein the thermal detector is configured to be responsive to a transient heating caused by absorbing modulated light.

35. A method for estimating a property of a fluid downhole, comprising:
   exposing the fluid to a light downhole; and
   using a thermal detector to sense changes in intensity of radiation from the fluid to estimate the property of the fluid, wherein the thermal detector is configured to be substantially non-responsive to a steady light and responsive to a modulated light.

* * * * *

UNITED STATES PATENT AND TRADEMARK OFFICE
CERTIFICATE OF CORRECTION

PATENT NO. : 7,423,258 B2  Page 1 of 1
APPLICATION NO. : 11/051388
DATED : September 9, 2008
INVENTOR(S) : Rocco DiFoggio and Paul Bergren It is certified that error appears in the above-identified patent and that said Letters Patent is hereby corrected as shown below:

Column 10, claim 3, line 41, delete "converting the changes", insert --converting changes--;

Column 11, claim 20, line 43, delete "analyzing the changes", insert --analyzing changes--;

Column 12, claim 25, line 1, delete "analyzing", insert --estimating--;

Column 12, claim 26, line 6, delete "analyzing", insert --estimating--;

Column 12, claim 27, line 8, delete "of reservoir", insert --of a reservoir--;

Column 12, claim 28, line 16, delete "analyzing the changes", insert --analyzing changes--;

Column 12, claim 31, line 27, delete "of reservoir", insert --of a reservoir--; and Column 12, claim 31, line 29, delete "through a reservoir", insert --through the reservoir--.

Signed and Sealed this

Seventeenth Day of March, 2009

JOHN DOLL
*Acting Director of the United States Patent and Trademark Office*